(12) United States Patent
Court et al.

(10) Patent No.: US 10,117,814 B2
(45) Date of Patent: Nov. 6, 2018

(54) ANHYDROUS ANTIPERSPIRANT AEROSOL COMPOSITIONS

(71) Applicant: Conopco, Inc., Englewood Cliffs, NJ (US)

(72) Inventors: Duncan Alexander Court, Wallasey (GB); Kevin Ronald Franklin, Wirral (GB); Philip Christopher Waterfield, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/520,615

(22) PCT Filed: Oct. 22, 2015

(86) PCT No.: PCT/EP2015/074529
§ 371 (c)(1),
(2) Date: Apr. 20, 2017

(87) PCT Pub. No.: WO2016/066528
PCT Pub. Date: May 6, 2016

(65) Prior Publication Data
US 2018/0015012 A1    Jan. 18, 2018

(30) Foreign Application Priority Data
Oct. 27, 2014 (EP) ..................... 14190530

(51) Int. Cl.
| A61K 8/26 | (2006.01) |
| A61K 8/44 | (2006.01) |
| A61K 8/31 | (2006.01) |
| A61K 8/20 | (2006.01) |
| A61K 8/891 | (2006.01) |
| A61K 8/41 | (2006.01) |
| A61K 8/04 | (2006.01) |
| A61Q 15/00 | (2006.01) |

(52) U.S. Cl.
CPC ............ *A61K 8/26* (2013.01); *A61K 8/046* (2013.01); *A61K 8/20* (2013.01); *A61K 8/31* (2013.01); *A61K 8/416* (2013.01); *A61K 8/44* (2013.01); *A61K 8/891* (2013.01); *A61Q 15/00* (2013.01); *A61K 2800/31* (2013.01)

(58) Field of Classification Search
None
See application file for complete search history.

(56) References Cited

U.S. PATENT DOCUMENTS

| 3,792,068 A * | 2/1974 | Luedders et al. ........ A61K 8/26 424/47 |
| 4,183,911 A | 1/1980 | Smithies et al. |
| 4,359,458 A | 11/1982 | Gosling et al. |
| 4,435,382 A | 3/1984 | Shin et al. |
| 5,744,130 A | 4/1998 | Guskey et al. |
| 5,955,065 A | 9/1999 | Thong et al. |
| 6,042,816 A | 3/2000 | Shen |
| 6,261,543 B1 | 7/2001 | Fletcher et al. |
| 6,511,243 B2 | 1/2003 | Miranda |
| 6,911,195 B2 | 6/2005 | Vu |
| 6,942,850 B2 | 9/2005 | Coe |
| 7,087,220 B2 | 8/2006 | Li |
| 7,704,531 B2 | 4/2010 | Tang et al. |
| 2003/0049219 A1 | 3/2003 | Lemoine et al. |
| 2003/0215399 A1 | 11/2003 | Smith et al. |
| 2004/0115147 A1 | 6/2004 | Vu et al. |
| 2005/0163737 A1 | 7/2005 | Lemoine et al. |
| 2006/0204463 A1 | 9/2006 | Tang et al. |
| 2006/0222612 A1 | 10/2006 | Ni et al. |
| 2007/0020211 A1 | 1/2007 | Li et al. |
| 2007/0196303 A1 | 8/2007 | Li et al. |
| 2007/0286830 A1 | 12/2007 | Li et al. |
| 2008/0131354 A1 | 6/2008 | Li |
| 2008/0241089 A1 | 10/2008 | Banowski et al. |
| 2008/0267895 A1 | 10/2008 | Franklin et al. |
| 2010/0303749 A1 | 12/2010 | Pan |
| 2011/0038823 A1 | 2/2011 | Phipps et al. |
| 2011/0038902 A1 | 2/2011 | Phipps et al. |
| 2011/0274637 A1 | 11/2011 | Milardovic et al. |
| 2014/0178321 A1 | 6/2014 | Banowski et al. |
| 2014/0301963 A1 | 10/2014 | Claas et al. |

FOREIGN PATENT DOCUMENTS

| CN | 1323191 | 11/2001 |
| EP | 0308937 | 3/1989 |
| EP | 0405598 | 1/1991 |

(Continued)

OTHER PUBLICATIONS

IPRP—Chapter II—PCT/EP2016/080034—Feb. 14, 2018 (9 pages) (Year: 2018).*
Pluronic(R) F-127, Newdruginfo.com, Jun. 7, 2016, 1 page.
Laden, Antiperspirants and Deodorants 1999 2nd Edition pp. 96-97,
Antiperspirants and Deodorants 1999 2nd Edition pp. 96-97, 1999, pp. 96-97, 2nd Edition.
IPRP2 in PCTEP2014059583, Sep. 11, 2015.
IPRP2 in PCTEP2014060306, Sep. 16, 2015.
IRPR2 in PCTEP2015074529, Dec. 2. 2016.
Search Report & Written Opinion in PCTEP2015074528, dated Jan. 20, 2016.
Search Report & Written Opinion in PCTEP2015074529, dated Dec. 21, 2015.

(Continued)

*Primary Examiner* — Aradhana Sasan
(74) *Attorney, Agent, or Firm* — Karen E. Klumas

(57) ABSTRACT

An anhydrous antiperspirant aerosol composition comprising a particulate antiperspirant active system, suspending agent, carrier oil, and liquefied propellant gas, characterized in that the particulate antiperspirant active system comprises an aluminum sesquichlorohydrate of formula $Al_2(OH)_{4.4}Cl_{1.6}$ to $Al_2(OH)_{4.9}Cl_{1.1}$ activated with a water soluble calcium salt.

12 Claims, No Drawings

(56) References Cited

FOREIGN PATENT DOCUMENTS

| | | |
|---|---|---|
| EP | 1175165 | 4/2000 |
| EP | 1104282 | 6/2001 |
| GB | 2113116 | 8/1983 |
| WO | WO0010512 | 3/2000 |
| WO | WO2008063188 | 5/2008 |
| WO | WO2009044381 | 4/2009 |
| WO | WO2009075678 | 6/2009 |
| WO | WO2009076592 | 6/2009 |
| WO | WO2011016807 | 2/2011 |
| WO | WO2012021356 | 2/2012 |
| WO | WO2012060817 | 5/2012 |
| WO | WO2012061280 | 5/2012 |
| WO | WO2012148480 | 11/2012 |
| WO | WO2012148481 | 11/2012 |
| WO | WO2013158077 | 10/2013 |
| WO | WO2014187684 | 11/2014 |
| WO | WO2014187685 | 11/2014 |

OTHER PUBLICATIONS

Search Report & Written Opinion in PCTEP2015076365, dated Feb. 11, 2016.
Search Report & Written Opinion in PCTEP2016080034, dated Feb. 9, 2017.
Search Report in EP13168417, dated Oct. 31, 2013.
Search Report in EP13168418, dated Oct. 31, 2013.
Search Report in EP14190530, dated Feb. 12, 2015.
Search Report in EP14190531, dated May 8, 2015.
Search Report in EP14193902, dated May 6, 2015.
Search Report in PCTEP2014059582, dated Oct. 6, 2014.
Search Report in PCTEP2014059583, dated Oct. 6, 2014.
Search Report in PCTEP2014060306, dated Oct. 6, 2014.
Written Opinion 1 in PCTEP2014059583, dated Oct. 6, 2014.
Written Opinion 2 in PCTEP2014059583, dated Apr. 30, 2015.
Written Opinion 2 in PCTEP2014060306, dated May 8, 2015.
Written Opinion in EP13168417, dated Oct. 31, 2013.
Written Opinion in EP13168418, dated Oct. 31, 2013.
Written Opinion in EP14190530, dated Feb. 12, 2015.
Written Opinion in EP14190531, dated May 8, 2015.
Written Opinion in EP14193902, dated May 6, 2015.
Written Opinion in PCTEP2014059582, dated Oct. 6, 2014.
Written Opinion 1 in PCTEP2014060306, dated Oct. 16, 2014.
Written Opinion in PCTEP2015074529, dated Sep. 6, 2016.
IRPR2 in PCTEP2015074528, Jan. 18, 2016.
Co-pending U.S. Appl. No. 14/889,866, Karim Mohamed Anwar M Fawz, filed Nov. 9, 2015.
Co-pending U.S. Appl. No. 14/889,874, Karim Mohamed Anwar M Fawz, filed Nov. 9, 2015.
Co-pending U.S. Appl. No. 15/520,652, Duncan Alexander Court, filed Apr. 20, 2017.
Co-pending U.S. Appl. No. 15/525,455, Kevin Ronald Franklin, filed May 9, 2017.
Co-pending U.S. Appl. No. 14/547,501, Kevin Ronald Franklin, filed Nov. 19, 2014.
Co-pending U.S. Appl. No. 14/889,863, Karim Mohamed Anwar F Fawz, filed Nov. 9, 2015.
Search Report and Written Opinion in EP17199987, dated Dec. 6, 2017.
IPRP in PCTEP2016080034, Feb. 14, 2018.

* cited by examiner

ANHYDROUS ANTIPERSPIRANT AEROSOL COMPOSITIONS

The present invention is concerned with antiperspirant compositions and with methods of making the same. It is particularly concerned with anhydrous aerosol compositions comprising basic aluminium chloride (herein BAC) antiperspirant actives.

Certain activated BAC actives are commercially available and their preparation and use are disclosed in numerous publications.

Traditionally, activated BAC samples have been prepared by prolonged heating of BAC solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated BAC samples have also been prepared using water soluble calcium acids, particularly with a further adjunct such as an amino acid, hydroxyl acid, or betaine. Some of these samples could be formulated into aqueous compositions without the antiperspirant losing all of its enhanced activity.

EP 1,104,282 (Gillette) discloses a means of producing activated BAC samples using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate BAC and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising BAC and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining BAC, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

WO 2009/075678, WO 2009/076592, WO 2011/016807, WO 2012/060817, WO 2012/061280, WO 2012/148480 and WO 2012/148481 (Colgate) disclose the manufacture of activated antiperspirant salts by neutralisation of aluminium chloride with calcium hydroxide in the presence of glycine.

The present invention is particularly concerned with BAC compositions comprising aluminium sesquichlorohydrate (herein ASCH) of chemical formula $Al_2(OH)_{4.4}Cl_{1.6}$ to $Al_2(OH)_{4.9}Cl_{1.1}$. This material is commercially available, but its formulation and use described herein are new and deliver unexpected benefits.

In a first aspect of the present invention, there is provided an anhydrous antiperspirant aerosol composition comprising a particulate antiperspirant active system, suspending agent, carrier oil, and liquefied propellant gas, characterised in that the particulate antiperspirant active system comprises an aluminium sesquichlorohydrate of formula $Al_2(OH)_{4.4}Cl_{1.6}$ to $Al_2(OH)_{4.9}Cl_{1.1}$ activated with a water soluble calcium salt.

In a second aspect of the present invention, there is provided a method of manufacture of a composition according to the first aspect of the invention.

In a third aspect of the present invention, there is provided a method of attaining an antiperspirant benefit comprising the topical application to the surface of the human body of a composition according to the first aspect of the invention.

The choice of BAC salt used is critical to the success of the present invention. We have found that surprisingly good results are found on using BAC salts commonly referred to as aluminium sesquichlorohydrate (herein ASCH) having the chemical formula $Al_2(OH)_{4.4}Cl_{1.6}$ to $Al_2(OH)_{4.9}Cl_{1.1}$. Most commercial ASCH samples are of chemical formula $Al_2(OH)_{4.7}Cl_{1.3}$ to $Al_2(OH)_{4.9}Cl_{1.1}$ and it is preferred to use BAC salts of this formula.

The surprisingly good results referred to in the above paragraph include surprisingly good antiperspirancy performance. In addition, compositions prepared according to the present invention have remarkable storage stability, maintaining their good performance for many months.

The BAC salt used in the present invention has aluminium to chloride molar ratio of from 1.25:1 to 1.82:1 and preferably 1.54:1 to 1.82:1.

The present invention involves the "activation" of ASCH by a water soluble calcium salt and preferably an amino acid.

In order for the ASCH to become activated, it is important to have sufficient calcium present relative to the amount of aluminium present. The molar ratio of calcium to aluminium is typically at least 1:40, preferably at least 1:30 and more preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar ratios of calcium to aluminium of at least 1:40 and at least 1:20, it is independently preferred that this ratio is no greater than 1:2 and more preferred that it is no greater than 1:5.

In particularly preferred embodiments, the molar ratio of calcium to aluminium is at least 1:15 and preferably no greater than 1:5 and in especially preferred embodiments it is at least 1:10 and preferably no greater than 1:5.

A preferred water soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In preferred embodiments, an amino acid is also used to activate the ASCH. The molar ratio of amino acid to aluminium is preferably at least 1:20, more preferably at least 1:10 and most preferably at least 1:5. It is not advantageous to have the amino acid concentration in excess of the aluminium concentration; hence, the molar amino acid to aluminium is preferably from 1:20 to 1:1, more preferably from 1:10 to 1:1 and most preferably from 1:5 to 1:1.

In particularly preferred embodiments, the molar ratio of amino acid to aluminium is at least 1:4 and preferably no greater than 1:1 and in especially preferred embodiments it is at least 1:3 and preferably no greater than 1:1.

The presence of both calcium and amino acid is highly preferred for the success of the present invention. In preferred embodiments, the molar ratio of calcium to aluminium is at least 1:40 and the molar ratio of amino acid to aluminium is at least 1:20. In further preferred embodiments the molar ratio of calcium to aluminium is at least 1:20 and the molar ratio of amino acid to aluminium is at least 1:10. In particularly preferred embodiments the molar ratio of calcium to aluminium is from 1:20 to 1:5 and the molar ratio of amino acid to aluminium is from 1:10 to 1:1.

In certain especially preferred embodiments, the molar ratio of calcium to aluminium is from 1:15 to 1:5 and the molar ratio of amino acid to aluminium is from 1:4 to 1:1. In these especially preferred embodiments, exemplary performance in is obtained when the molar ratio of calcium to aluminium is from 1:10 to 1:5 and the molar ratio of amino acid to aluminium is from 1:3 to 1:1.

The above indicated preferences for calcium to aluminium molar ratio and/or amino acid to aluminium molar ratio lead to compositions of higher Band III content (vide infra) and, in general, higher antiperspirancy performance. It will be noted that higher Band III content is generally indicative of higher antiperspirancy performance.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

In preferred embodiments of the invention, the aluminium sesquichlorohydrate in the particulate antiperspirant active system has a Band III content of at least 40%; in particularly preferred embodiments, the Band III content of the aluminium sesquichlorohydrate is at least 55%.

In the activation process and method of manufacture described herein, it is preferred that the activation mixture is heated sufficiently for the Band III content of the aluminium species to become at least 40% and more preferably at least 55%.

In a method of manufacture according to the invention, an aqueous solution of aluminium sesquichlorohydrate of formula $Al_2(OH)_{4.4}Cl_{1.6}$ to $Al_2(OH)_{4.9}Cl_{1.1}$ is heated with a water soluble calcium salt to achieve a Band III content of at least 40% before being spray dried to give a powder which is subsequently formulated with a suspending agent, carrier oil and liquefied propellant gas.

In a preferred method of manufacture as described in the above paragraph, the solution of aluminium sesquichlorohydrate and water soluble calcium salt is also heated with an amino acid. In a particularly preferred aspect of this method, the aluminium sesquichlorohydrate is heated to achieve a Band III content of at least 55%.

The particulate antiperspirant active system used in the present invention may typically be considered to be a co-spray-dried mixture of (i) aluminium sesquichlorohydrate of formula $Al_2(OH)_{4.4}Cl_{1.6}$ to $Al_2(OH)_{4.9}Cl_{1.1}$ activated by calcium chloride and (ii) the calcium chloride used to achieve said activation. Preferably, the antiperspirant active system may be considered to be a co-spray-dried mixture of (i) aluminium sesquichlorohydrate of formula $Al_2(OH)_{4.4}Cl_{1.6}$ to $Al_2(OH)_{4.9}Cl_{1.1}$ activated by calcium chloride and an amino acid and (ii) the calcium chloride and amino acid used to achieve said activation.

The spray-dried powder produced from the aqueous solution of an activated antiperspirant salt is the particulate antiperspirant active "system" as described in the first aspect of the invention.

The particulate antiperspirant active system preferably has a mean particle size (D50) of at least 6 microns, more preferably at least 17 microns, and most preferably from 20 to 30 microns. Such compositions have been found to give surprisingly good antiperspirancy performance.

Herein, mean (D50) particle sizes may be measured using (laser) light scattering techniques, for example using a Mastersizer instrument, obtainable from Malvern Instruments. Such instruments are set to produce a volume plot and a lens is selected in accordance with the maker's instructions to accommodate the expected particle size distribution, (or various lenses can be tested until the best lens is identified). Measurements are made by methods known in the art.

The particulate antiperspirant active system is preferably spray-dried using rotary atomisation.

The compositions of the present invention are anhydrous, having less than 1% by weight of free water and preferably less than 0.1% by weight of free water.

Herein, "free water" excludes any water of hydration associated with the antiperspirant salt or other component added to a particular composition, but includes all other water present.

Other non-essential components may also be including in compositions according to the invention.

Herein, amounts and concentrations of ingredients are percentages by weight of the total composition, unless otherwise indicated and ratios are ratios by weight, unless otherwise indicated.

A suspending agent is an essential component of compositions of the invention. Such agents aid the suspension of the particulate antiperspirant active system in the composition. Preferred suspending agents are clays, particularly hydrophobically modified clays. Particularly preferred are hydrophobically modified hectorite or bentonite clays and especially preferred is disteardimonium hectorite (e.g. Bentone 38V, ex Elementis).

The suspending agent is typically employed at from 0.1 to 1.5% by weight of the total composition.

Propylene carbonate may also be advantageously employed in compositions of the present invention, typically at from 0.001 to 0.1% by weight.

A liquefied propellant gas is an essential component of compositions of the invention. Preferred liquefied propellant gases are hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquefied hydrocarbon gases, and especially $C_3$ to $C_6$ hydrocarbons, including propane, butane, isobutane, pentane and isopentane and mixtures of two or more thereof. Of these especially preferred propellants, isobutane, isobutane/propane, butane/propane and mixtures of propane, isobutane and butane are most preferred.

The liquefied propellant gas is typically the major component of aerosol compositions, often comprising from 30 to 99% weight and preferably comprising from 50 to 95% by weight.

An essential component of compositions of the invention is a carrier oil. In preferred embodiments, this may also be a masking oil, serving the purpose of reducing visible deposits when the composition accidentally comes into contact with clothing, for example.

Herein, the terms "oil" and signifies a water-insoluble organic material that is liquid at 20° C. Any material having a solubility of less than 0.1 g/100 g at 20° C. is considered to be insoluble.

A preferred optional component for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of carrier oil in the composition is preferably from 0.1 to 20%, more preferably from 0.5 to 10%, and most preferably at from 2 to 8% by weight of the total composition. In certain preferred embodiments the carrier oil is present at greater than 2.5% and less than 6% by weight of the total composition.

The carrier oil may be selected from any of those known in the art, although hydrophobic carrier oils are preferred.

A preferred class of carrier oil are silicone oils, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202.

Suitable carrier oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable carrier oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable carrier oils can include those derived from unsaturated $C_{18}$ acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable carrier oils, that can also be emollient oils, comprise alkyl or alkyl-aryl ester oils having a boiling point of above 150° C. (and a melting point of below 20° C.).

Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable carrier oils comprises non-volatile dimethicones, often comprising phenyl or diphenylene substitution, for example Dow Corning 200 350 cps or Dow Corning 556.

EXAMPLES

In the following examples, all percentages are by weight, unless otherwise indicated.

The ASCH used was approximately 80% anhydrous ASCH solids (and 20% water) and was obtained from Summit as Reach 301.

Example 1 as detailed in Table 1 was prepared by the following process. 15 parts of Reach 301 powder, 1.5 parts anhydrous calcium chloride and 4.7 parts glycine were combined with 72.6 parts water at room temperature. The solution was heated at 85° C. for 18 hours in sealed 1 L jars. The solution resulting from the above process was spray-dried using a bench-top Lab-Plant-05 spray dryer (inlet temperature 250°, outlet temperature 112+/−1°, jet atomisation).

The particulate AASCH obtained from the above process had a mean (D50) particle size of 7.2 microns, a Band III content of 61%, and a ratio of Band II to Band III of 1:6.65. It comprised 18.6% Al, 2.7% Ca, and 25.1% glycine.

The particulate AASCH was formulated with the other components indicated in Table 1 by methods known in the art. Example 1 comprised 7.07% of the particulate AASCH, having the amounts of ASCH, calcium chloride, and glycine as indicated in Table 1. The balance was water associated with the AASCH powder.

Comparative Example A was prepared by methods known in art. The antiperspirant active (Reach 103, ex Summit) had a Band III content of 29% and a Band II:III ratio of 1:0.55. 5.00% of this active was used, corresponding to 4.5% anhydrous ASCH solids.

TABLE 1

Example 1 and Comparative Example A

| Component | | | % w/w | |
|---|---|---|---|---|
| Trade name | INCI name | Supplier | 1 | A |
| ASCH | Aluminium sesquichlorohydrate | Summit | 4.38 | 4.50 |
| Anhydrous calcium chloride | Calcium chloride | Sigma-Aldrich | 0.53 | — |
| Glycine | Glycine | Sigma-Aldrich | 1.77 | — |
| DC245 | Cyclomethicone | Dow Corning | 2.38 | 3.49 |
| Bentone 38V | Disteardimomonium hectorite | Elementis UK | 0.50 | 0.50 |
| Propylene carbonate | Propylene carbonate | Sigma-Aldrich | 0.01 | 0.01 |
| Fluid AP | PPG-14 butyl ether | Amerchol Corp. | 2.04 | 3.00 |
| AP40 | Butane/isobutene/propane | Harp International | 87.00 | 87.00 |
| Fragrance | Parfum | IFF | 1.00 | 1.00 |

Sweat Weight Reduction (SWR) results were obtained using a test panel of 30 female volunteers. Test operators applied Example 1 (2 seconds spray, ca 2 g applied) to one axilla and a non-antiperspirant deodorant body spray (2 seconds spray, ca 1.4 g applied) to the other axilla of each panellist. This was done once each day for three days. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The SWR for each panellist was calculated as a percentage (% SWR) and the mean % SWR was calculated according to the method described by Murphy and Levine in "Analysis of Antiperspirant Efficacy Results", *J. Soc. Cosmetic Chemists,* 1991 (May), 42, 167-197.

It was found that Example 1 gave a SWR that was 48% greater than the control deodorant body spray.

In a further SWR test, Comparative Example A was assessed against the same control deodorant body spray. Comparative Example A gave a SWR that was 26% greater than the control deodorant body spray, i.e. a considerably lesser reduction than that obtained by use of Example 1.

Example 2 as detailed in Table 2 was prepared by the following process. 15 parts of Reach 301 powder and 0.9 parts anhydrous calcium chloride were combined with 84.1 parts water at room temperature. The solution was heated at 85° C. for 18 hrs in sealed 1 L jars. The solution resulting from the above process was spray-dried using a bench-top Lab-Plant-05 spray dryer.

The particulate AASCH obtained from the above process had a Band III content of 37%, and a ratio of Band II to Band III of 1:1.06. It comprised 22.9% Al, 1.9% Ca, and 0% glycine.

The particulate AASCH was formulated as indicated in Table 1 by methods known in the art. Example 2 comprised 5.00% of the spray-dried AASCH, having the amounts of amounts of ASCH and calcium chloride as indicated in Table 3. The balance was water associated with the AASCH powder.

Comparative Example B as detailed in Table 2 was prepared by the following process. 30 parts of Chlorhydrol 50 (50% aqueous ACH) and 0.9 parts anhydrous calcium chloride were combined with 68.5 parts water at room temperature. The solution was heated at 85° C. for 18 hours in sealed 1 L jars and the resulting hot solution was immediately spray-dried using a bench-top Lab-Plant-05 spray dryer. The resulting powder was formulated at 5.00% (including a small amount of associated water) with the other components using methods known in the art.

TABLE 2

| Component | | | % w/w | |
|---|---|---|---|---|
| Trade name | INCI name | Supplier | 2 | B |
| ASCH | Aluminium sesquichlorohydrate | Summit | 3.82 | — |
| Anhydrous calcium chloride | Calcium chloride | Sigma-Aldrich | 0.27 | 0.29 |
| ACH | Aluminium chlorohydrate | Summit | — | 4.71 |
| DC245 | Cyclomethicone | Dow Corning | 3.49 | 3.49 |
| Bentone 38V | Disteardimomonium hectorite | Elementis UK | 0.50 | 0.50 |
| Propylene carbonate | Propylene carbonate | Sigma-Aldrich | 0.01 | 0.01 |
| Fluid AP | PPG-14 butyl ether | Amerchol Corp. | 3.00 | 3.00 |
| AP40 | Butane/isobutene/propane | Harp International | 87.00 | 87.00 |
| Fragrance | Parfum | IFF | 1.00 | 1.00 |

SWR results were obtained using a test panel and method as described above. Example 2 gave a SWR) that was 44% greater than the control deodorant body spray and Comparative Example B gave a SWR that was 36% greater than the control deodorant body spray. These results show the superiority of compositions according to the invention over those prepared using ACH "activated" with a water soluble calcium salt.

Example 3 as detailed in Table 3 was prepared by the following process.

30 parts of Reach 301 powder, 4.0 parts calcium chloride dihydrate and 9.4 parts glycine were combined with 56.6 parts water. 60 L of this solution was heated at 85° C. and then maintained at this temperature for 5 hours in a corrosion resistant 70 L vessel.

The resulting solution was spray-dried using a large scale spray dryer (inlet temperature 290+/−5°, outlet temperature 117+/−2°, rotary atomisation).

The particulate AASCH obtained from the above process had a mean (D50) particle size of 27 microns, a Band III content of 66%, and a ratio of Band II to Band III of 1:7.13. It comprised 19.3% Al, 2.8% Ca, and 26.0% glycine.

The particulate AASCH was formulated as indicated in Table 3 by methods known in the art. Like Example 1, Example 3 comprised 7.07% of the spray-dried AASCH, having the amounts of amounts of ASCH, calcium chloride, and glycine as indicated. The balance was water associated with the AASCH powder.

TABLE 3

| Example 3 | | | |
|---|---|---|---|
| Component | | | |
| Trade name | INCI name | Supplier | % w/w |
| ASCH | Aluminium sesquichlorohydrate | Summit | 4.55 |
| Anhydrous calcium chloride | Calcium chloride | Sigma-Aldrich | 0.55 |
| Glycine | Glycine | Sigma-Aldrich | 1.83 |
| DC245 | Cyclomethicone | Dow Corning | 2.38 |
| Bentone 38V | Disteardimomonium hectorite | Elementis UK | 0.50 |
| Propylene carbonate | Propylene carbonate | Sigma-Aldrich | 0.01 |
| Fluid AP | PPG-14 butyl ether | Amerchol Corp. | 2.04 |
| AP40 | Butane/isobutene/propane | Harp International | 87.00 |
| Fragrance | Parfum | IFF | 1.00 |

SWR results were again obtained using a test panel and method as described above and Example 3 gave a SWR that was 58% greater than the control deodorant body spray.

Examples 4 and 5 as described in Table 4 were prepared as follows.

For Example 4, 30 parts of Reach 301 powder, 1.8 parts calcium chloride dihydrate and 4.0 parts glycine were combined with 64.2 parts water. 60 L of this solution was heated at 85° C. and then maintained at this temperature for 5 hours in a corrosion resistant 70 L vessel.

The resulting solution was spray-dried using a large scale spray dryer (inlet temperature 290+/−5°, outlet temperature 117+/−2°, rotary atomisation).

The particulate AASCH obtained from the above process had a mean (D50) particle size of 28.5 microns, a Band III content of 53.8%, and a ratio of Band II to Band III of 1:2.13. It comprised 22.0% Al, 1.9% Ca, and 12.8% glycine.

The particulate AASCH was formulated as indicated in Table 4 by methods known in the art. Example 4 comprised 5.97% of the spray-dried AASCH, having the amounts of amounts of ASCH, calcium chloride, and glycine as indicated in Table 4. The balance was water associated with the AASCH powder.

Example 5 was prepared using the same spray-dried AASCH powder as used for Example 3, using methods known in the art. 4.24% of the AASCH was employed, having the amounts of amounts of ASCH, calcium chloride, and glycine as indicated in Table 4. The balance was water associated with the AASCH powder.

Comparative Example C was prepared using 5.00% activated aluminium chlorohydrate (Summit 7167; 85% anhydrous AACH) using methods known in the art. This material had a Band III content of 41.6% and a Band II:III ratio of 1:0.91.

TABLE 4

| Component | | | % w/w | | |
|---|---|---|---|---|---|
| Trade name | INCI name | Supplier | 4 | 5 | C |
| ASCH | Aluminium sesquichloro-hydrate | SummitReheis | 4.38 | 2.73 | — |
| Anh. calcium chloride | Calcium chloride | Sigma-Aldrich | 0.32 | 0.33 | — |
| Glycine | Glycine | Sigma-Aldrich | 0.76 | 1.10 | — |
| AACH | | | | | 4.25 |
| DC245 | Cyclomethicone | Dow Corning | 2.515 | 5.21 | 5.21 |
| Bentone 38V | Di-steardimomonium hectorite | Elementis UK | 0.500 | 0.50 | 0.50 |
| Propylene carbonate | Propylene carbonate | Sigma-Aldrich | 0.015 | 0.01 | 0.01 |
| Fluid AP | PPG-14 butyl ether | Amerchol Corp. | 3.000 | 2.04 | 2.04 |
| AP40 | Butane/isobutene/propane | Harp International | 87.000 | 87.00 | 87.00 |
| Fragrance | Parfum | IFF | 1.000 | 1.00 | 1.00 |

SWR results were obtained using a test panel and method as described above. Example 4 gave a SWR that was 58% greater than the control deodorant body and Example 5 gave a SWR that was 53% greater than the control. Comparative Example C gave a SWR that was 30% greater than the control. These results show the superiority of compositions according to the invention over those prepared using 'conventional' heat-activated AACH.

The invention claimed is:

1. An anhydrous antiperspirant aerosol composition comprising a particulate antiperspirant active system, suspending agent, carrier oil, and liquefied propellant gas, wherein particulate antiperspirant active system comprises an aluminium sesquichlorohydrate of formula $Al_2(OH)_{4.4}Cl_{1.6}$ to $Al_2(OH)_{4.9}Cl_{1.1}$ activated with a water soluble calcium salt and an amino acid, and wherein the molar ratio of amino acid to aluminium is from 1:5 to 1:1, and the amino acid is glycine.

2. The composition according to claim 1, wherein the aluminium sesquichlorohydrate the particulate antiperspirant active system has a Band III content of at least 40%.

3. The composition according to claim 2, wherein the aluminium sesquichlorohydrate in the particulate antiperspirant active system has a Band III content of at least 60%.

4. The composition according to claim 2, wherein the aluminium sesquichlorohydrate in the particulate antiperspirant active system has a Band III to Band II ratio of 2:1 or greater.

5. The composition according to claim 4, wherein the aluminium sesquichlorohydrate in the particulate antiperspirant active system has a Band III to Band II ratio of 5:1 or greater.

6. The composition according to claim 1, wherein the aluminium sesquichlorohydrate in the particulate antiperspirant active system has a molar ratio of calcium to aluminium of at least 1:20.

7. The composition according to claim 6, wherein the aluminium sesquichlorohydrate in the particulate antiperspirant active system has a molar ratio of calcium to aluminium of at least 1:15 and the molar ratio of amino acid to aluminium is from 1:4 to 1:1.

8. A method of manufacture of an antiperspirant composition according to claim 1, wherein an aqueous solution of aluminium sesquichlorohydrate of formula $Al_2(OH)_{4.4}Cl_{1.6}$ to $Al_2(OH)_{4.9}Cl_{1.1}$ is heated with a water soluble calcium salt and amino acid to achieve a Band III content of at least 40% before being spray dried to give a powder which is subsequently formulated with a suspending agent, carrier oil and liquefied propellant gas.

9. The method according to claim 8, wherein the solution of aluminium sesquichlorohydrate of formula $Al_2(OH)_{4.4}Cl_{1.6}$ to $Al_2(OH)_{4.9}Cl_{1.1}$ is heated with a water soluble calcium salt and an amino acid- to achieve a Band III content of at least 55% before it is spray dried.

10. The method according to claim 8, wherein the powder is of a mean (D50) particle size that is from 20 to 30 microns before being formulated with the suspending agent, carrier oil and liquefied propellant gas.

11. The method according to claim 8, wherein the water soluble calcium salt is calcium chloride.

12. The method according to claim 8, wherein the aluminium sesquichlorohydrate of formula $Al_2(OH)_{4.7}Cl_{1.3}$ to $Al_2(OH)_{4.9}Cl_{1.1}$.

* * * * *